United States Patent [19]
Toy et al.

[11] 3,937,765
[45] Feb. 10, 1976

[54] PROCESS FOR PREPARING O,O-DIARYL N,N-DIALKYL PHOSPHORAMIDATES

[75] Inventors: Arthur D. F. Toy, Stamford, Conn.; Kenneth L. Eilers, Irvington, N.Y.

[73] Assignee: Stauffer Chemical Company, New York, N.Y.

[22] Filed: Oct. 12, 1970

[21] Appl. No.: 80,195

[52] U.S. Cl. ................................ 260/973; 428/921
[51] Int. Cl.$^2$ ..................... C07F 9/24; D06C 27/00
[58] Field of Search ..................................... 260/973

[56] References Cited
UNITED STATES PATENTS

| | | | |
|---|---|---|---|
| 2,520,393 | 8/1950 | Fletcher | 260/973 X |
| 2,944,933 | 7/1960 | Sallmann | 260/973 X |
| 2,994,638 | 8/1961 | Malz et al. | 260/973 X |

*Primary Examiner*—Anton H. Sutto

[57] ABSTRACT

Flame retardant compounds, O,O-diaryl N,N-dialkyl phosphoramidates are prepared by reacting a phosphoramidohalidate or a phosphoramidic dihalide with a phenol in the presence of an alkali or alkaline earth metal hydroxide and a water-insoluble, water-immiscible, non-hydroxylic polar ketone which is a solvent for both the reactants and the product. High yields are obtained.

10 Claims, No Drawings

PROCESS FOR PREPARING O,O-DIARYL N,N-DIALKYL PHOSPHORAMIDATES

The present invention relates to a new process for preparing O,O-diaryl N,N-dialkyl phosphoramidates which are useful as flame retardants.

BACKGROUND OF THE INVENTION

Phosphoramidates, e.g., $(RO)_2P(O)N(R)_2$ wherein R is alkyl, are known compounds. These compounds have been prepared by reacting primary and secondary amines with phosphoric halides, substituted phosphoric halides, and organic halophosphates. These reactions are basically carried out in inert solvents such as ethers at low temperatures and the products are isolated after the separation of the amine salt by-product. The unsubstituted phosphoramidate $(RO)_2P(O)NH_2$ and particularly the diaryl phosphoramidate is a known compound (U.S. Pat. No. 3,240,729). This compound is an effective reactive flame retardant for use in preparing polyurethanes. These compounds are, however, unstable in caustic solution thereby rendering them undesirable for use in rayon spinning solutions. This problem has been unexpectedly overcome by forming the O,O-diaryl N,N-dialkyl phosphoramidate. This is claimed in the co-pending application of Eilers and Toy filed concurrent herewith.

In attempting to prepare O,O-diaryl N,N-dialkyl phosphoramidates by known routes numerous problems were encountered which were of significance to the commercial development of an economically competitive product. One of the processes investigated involves the reaction between a diaryl phosphorohalidate and a 100% excess of dialkyl amine. While quantitative yields of high purity in the reaction flask can be obtained, quantitative isolation of the final phosphoramidate product is not easily attained. Also, problems exist in the preparation of the diaryl phosphorohalidate intermediate.

Firstly, the diaryl phosphorohalidate, such as diphenyl phosphorochloridate (used hereinafter as exemplary) in alternatively prepared by chlorinating diphenyl hydrogen phosphonate or by the Todd process, the details of which are set forth more fully hereinafter. In chlorinating the phosphonate, hydrogen chloride is evolved as a by-product. The hydrogen chloride is soluble in the diphenyl phosphorochloridate making its removal difficult. Isolation of the pure compound without combination is, therefore, difficult. The economics of the final product require inexpensive starting materials. Low yields of the starting material raise its cost and tend to destroy the economics of the process.

A further problem is encountered when the phosphorochloridate is reacted with a secondary dialkyl amine. As a by-product of the reaction there is formed one mole of dialkyl amine hydrochloride per mole of product. This material flocculates and is extremely difficult to separate from the final product. Once the floc is separated, it is difficult and expensive to dispose of. For instance, dimethyl amine is an expensive reactant, and one extra mole of this amine is required for each mole of product. The loss of the amine in the by-product is economically unattractive. If the floc comes into contact with caustic, the dimethyl amine can be regenerated. Since the dimethyl amine is toxic, waste disposal techniques must, therefore, be carefully controlled. Regeneration and recycling of the amine is uneconomical and impractical.

The Todd process involves the reaction of the diaryl hydrogen phosphonate with a 100% excess of dialkyl amine in the presence of an excess of perchlorinated alkane, such as carbon tetrachloride. This process is even more costly than above and incurs basically the same disadvantages as the process discussed above.

It has now been found that these difficulties can be overcome and O,O-diaryl N,N-dialkyl phosphoramidates can be easily prepared by the new process of the present invention. The compounds as prepared by this new process find use as flame retardant agents in polymer compositions.

THE INVENTION

In accordance with the present invention, it has now been unexpectedly found that O,O-diaryl N,N-dialkyl phosphoramidates of the formula:

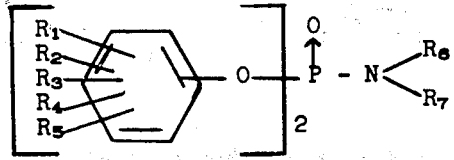

wherein $R_1$, $R_2$, $R_3$, $R_4$, and $R_5$ are the same or different radicals independently selected from the group consisting of hydrogen, alkyl, and hydroxyalkyl of from 1 to 4 carbon atoms, phenyl, alkoxy wherein the alkyl group has from 1 to 4 carbon atoms, chlorine, bromine, chloroalkyl or bromoalkyl of from 1 to 4 carbon atoms, and wherein $R_6$ and $R_7$ are the same or different allyl radicals of from 1 to 4 carbon atoms can be easily prepared by reacting a dialkyl phosphoramidic dihalide with a phenol in the presence of an alkali or alkaline earth metal hydroxide and a ketone solvent which is a solvent for both the reactants and the product. The ketone solvent is characterized as being a water-insoluble, water-immiscible, non-hydroxylic, polar compound. The use of the solvent prevents the formation of undesirable halide by-products and hydrolysis by-products which cleave the amine group from the phosphorus atom causing the reaction to cease. Hydrolysis of the products is also inhibited. It was unexpectedly found that the use of such a solvent prevents the hydrolysis of the phosphoramidic halides by the aqueous sodium hydroxide solution. It also permits a more complete reaction between the dialkyl phosphoramidic halide, the phenol, and the sodium hydroxide.

It has further been found that the alkali or alkaline earth metal hydroxide can be used in the absence of water with the ketone solvent. In the absence of the ketone solvent, aqueous sodium hydroxide would cause partial hydrolysis of the dialkyl phosphoramidic halide. This would result in a reduction in yield of the final desired product, the O,O-diaryl N,N-dialkyl phosphoramidate.

As water has a critical effect on the reaction system, weak hydroxide solutions are less preferred to concentrated solutions of at least 25% hydroxide, and preferably above 50%. Most preferably, no water is present in the reaction mixture and therefore it is preferable to add the alkali or alkaline earth metal hydroxide in solid form directly to the reaction mixture.

The water content of the reaction system, while detrimental to the formation of the pure O,O-diaryl N,N-dialkyl phosphoramidate, is useful in forming mixed aryl materials. By controlling the water content of the reaction system as well as the stoichiometric quantities of the reactants, the process of the invention can provide large quantities of monoaryl N,N-dialkyl phosphoramidic monochloride, such as O-phenyl N,N-dimethyl phosphoramidochloridate. The process could then be repeated using a different aryl reactant such as cresol or xylenol. A mixed phenyl-cresyl or phenyl-xylenyl product could thereby be obtained.

The N,N-dialkyl phosphoramidic halides which can be used in the process of the present invention correspond to the formula:

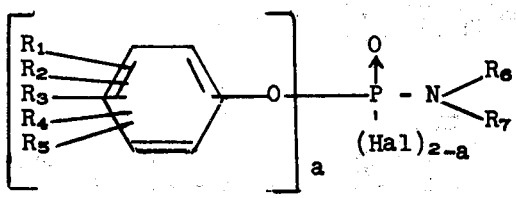

wherein $R_1$-$R_7$ are as defined hereinbefore, a is a number equal to 1 or 0 and hal is a halogen of chlorine or bromine. When a is 1, a mixed phenol product can be prepared. As used herein the term N,N-dialkyl phosphoramidic halide is intended to include both the phosphoramidohalidate (a=1) as well as the phosphoramidic dihalide (a=0). Preferably, a is zero (0), and the phosphoramidic halide is the dihalide and corresponds to the formula:

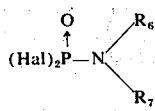

wherein Hal and $R_6$ and $R_7$ are as defined hereinbefore. Illustrative of these compounds are the dimethyl, diethyl, dipropyl, and dibutyl phosphoramidic dichlorides and dibromides. Also, the mixed amides such as the methyl ethyl, methyl propyl, ethyl propyl, ethyl butyl, and propyl butyl phosphoramidic dichlorides and dibromides can also be used. Mixtures of dihalides can also be used, if desired. Also, mixed monochloro monobromo compounds could be used but, as these compounds are more expensive, would be less attractive economically. The foregoing are given as illustrative and the invention is not intended to be limited thereto.

The further discussion of the invention will be made in reference to the preferred phosphoramidic dihalide species though the discussion is equally applicable to the phosphorochloridate species.

The phenol which is used in the present invention corresponds to the formula:

wherein $R_1$-$R_5$ are as defined hereinbefore. The terms "phenol" and "phenols" as used herein are used under the broad meaning of the terms to cover arylhydroxides except where it is clear from the context of the discussion that the specific compound "hydroxybenzene" is being referred to. Preferably, the compound which is used in the reaction is phenol though other compounds such as cresylic acid, xylenol, ethylphenol, propylphenol, butylphenol, phenylphenol, thymol, chlorophenic acid, hydroxyethylphenol, creosol, monobromophenol, guaiacol, and the like can also be used.

The phenol is used in an amount stoichiometrically equivalent to the phosphoramidic halide and preferably in slight excess. Generally, two moles plus a slight excess of the phenol are used per mole of phosphoramidic dihalide so as to provide the pure diaryl compound. It has been found that extremely effective results are obtained when 2.05 moles of phenol are used per mole of phosphoramidic dihalide. Mixed esters can be made by controlling the water content of the reaction as well as the stoichiometric quantities of the phenol. Based on the weight percent of hydroxide in the water, at 25% YOH the amount of the monohalide prepared ranges from about 40 to about 50%; at 50% YOH, the percentage of monohalide decreases to less than 10% (about 5%) and at 100% YOH only traces of monohalide are found. (Y=alkali or alkaline earth metal).

The phosphoramidic dihalide and the phenol are reacted in the presence of a ketone. The ketone must be a solvent for the phosphoramidic dihalide, the phenol, and the O,O-diaryl N,N-dialkyl phosphoramidate. The ketone must also be water-insoluble, e.g., less than 5 grams and preferably less than 1 gram per 100 grams of water, polar and non-hydroxylic. To facilitate reaction, the ketone should normally be a liquid (at room temperature) and have a boiling point of under 200°C. Surprisingly, the desired reaction does not proceed in the absence of the solvent and only partially in the presence of other organic solvents such as toluene.

The ketones which can be used in the present invention correspond to the formula:

wherein $R_x$ is a $C_1$-$C_4$ alkyl and $R_y$ is a $C_3$-$C_8$ alkyl, the total number of carbon atoms in the ketone not to exceed 10. The ketones can be simple (symmetrical) or mixed, e.g., $R_x$ and $R_y$ can be the same or different. Also, mixed solvent systems using 2 or more different ketones can also be used. Illustrative of the ketones which can be used are:

di-n-propyl ketone
diisopropyl ketone
di-n-butyl ketone
diisobutyl ketone
di-sec-butyl ketone
methyl n-propyl ketone
methyl isopropyl ketone
methyl n-butyl ketone
methyl isobutyl ketone
methyl sec-butyl ketone
pinacolone
methyl n-amyl ketone
methyl n-hexyl ketone
6-methyl-2-heptanone
methyl n-heptyl ketone
methyl n-octyl ketone
ethyl n-propyl ketone
ethyl n-butyl ketone
propyl isopropyl ketone
ethyl isobutyl ketone Alicyclic ketone of the formula:

CH₂(CH₂)ₙC O wherein $n$ is an integer of 4 or 5 and wherein the hydrogens can be replaced with non-interfering groups such as $C_1$-$C_4$ lower alkyl groups can also be used. The total carbon content preferably does not exceed 10. The ketones can be illustrated by cyclohexanone, 2-methylcyclohexanone, and cycloheptanone. The foregoing are given as illustrative of the ketones which can be used in the present invention and the invention is in no way intended to be limited thereto. Preferably, the ketone used is methyl isobutyl ketone.

The ketone is used in an amount sufficient to prevent caking of the by-product salt Na-Hal. Effective results are obtained when using the ketone in amounts of at least 1 liter, and preferably about 2 liter of ketone per mole of phosphoramidic dihalide.

In general, the process of the invention is accomplished by dissolving the phosphoramidic dihalide and the phenol in the ketone in a flask or kettle which is equipped with a stirrer. For effective results, the phenol is used in slight molar excess (2.05) per mole of phosphoramidic dihalide. The ketone solvent is generally used in an amount sufficient to provide at least one liter ketone per mole of phosphoramidic dihalide. The hydroxide which is used in the present reaction can be any of the alkali metal hydroxides and the alkaline earth metal hydroxides. Included within the term alkali metal hydroxides are the alkaline earth metal oxides. Illustrative of these compounds are sodium, potassium and lithium hydroxides, calcium oxide (lime), calcium hydroxide (slaked lime), strontium oxide and hydroxide, hydrous strontium hydroxide, barium oxide, and barium hydroxide. The hydroxide is to be utilized in an amount at least stoichiometrically equivalent to the phenol used. Preferably, the sodium hydroxide is used in slight excess, e.g., 2.10 moles sodium hydroxide per 2.05 moles phenol per 1 mole of phosphoramidic dihalide. The preferred hydroxide is sodium hydroxide. The remainder of the discussion of the present invention will be in reference to the specific compound sodium hydroxide as illustrative though the teachings will be applicable to the other listed hydroxides as well.

The hydroxide which is used in the reaction is preferably in the form of small particles such as thin flakes or ground pellets. Since the hydroxide is critical to and enters into the overall reaction, it is preferable that the hydroxide be used in a form which has a large a surface area as possible to facilitate reaction.

The temperature of the reaction should be maintained at an effective reaction level. Temperatures within the range of 25°-60°C. have been found to be effective though generally temperatures between 40° and 50° are preferred. Higher temperatures are less preferable as hydrolysis of the product and the phosphoramidic dihalide starting material increases as the temperature increases. Since the reaction is exothermic, control of temperature may be accomplished by external cooling such as circulating brine or on an ice bath.

The reaction proceeds fairly rapidly and with phosphoramidic dihalides having lower alkyl substituents on the nitrogen the reaction is completed within about 2 hours. Less reactive phosphoramidic dihalides having higher alkyl substituents on the nitrogen may require additional reaction time.

Upon completion of the reaction, the product is washed with water. The reaction by-product is sodium halide which appears as a fine suspension in the ketone. The suspension is so fine that the sodium halide does not settle out and must be separated. This can be effectively accomplished by washing. The sodium halide will readily dissolve in the water even up to the saturation point. Thus, only as much water as is necessary to dissolve the theoretical amount of salt by-product need be used. The water can be drawn off the bottom in a separatory funnel. The product is generally washed until the salt and other basic components have been removed, e.g., until a pH of about 8 is attained in the wash water.

While separation of the salt impurity by dissolution proves to be an effective laboratory technique, other mechanical and chemical separation methods such as centrifuging might find more effective use in an industrial plant.

After separating the salt, the product in the O,O-diaryl N,N-dimethyl phosphoramidate is isolated from the ketone. The most practical method is to distill off the ketone and recycle the ketone for the next reaction.

The compounds which can be prepared in accordance with the present invention are O,O-diaryl N,N-dialkyl phosphoramidates of the formula:

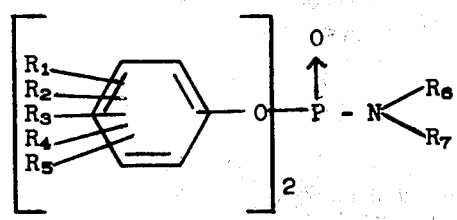

wherein the $R_1$ through $R_5$ groups can be the same or different and an R group of one of the two aryl rings is not required to correspond to the similarly numbered R group on the other aryl ring, and $R_6$ and $R_7$ are $C_1$-$C_4$ alkyl radicals. The $R_1$ through $R_5$ groups can be and are preferably hydrogen. $R_1$-$R_5$ can also be halogen such as chlorine and bromine, $R_1$-$R_5$ can be $C_1$-$C_4$ alkyl such as methyl, ethyl, propyl, isopropyl, butyl, and tert-butyl. The alkyl compounds are intended to include substituted derivatives thereof.

Illustrative of the compounds which can be prepared by the process of the invention are:

O,O-diphenyl N,N-dimethyl phosphoramidate
O,O-dicresyl N,N-dimethyl phosphoramidate
O,O-dixylyl N,N-dimethyl phosphoramidate
O,O-diphenyl N,N-diethyl phosphoramidate
O,O-bis(ethylphenyl) N,N-dipropyl phosphoramidate
O-phenyl, O'-cresyl N,N-dimethyl phosphoramidate
O-cresyl, O'-xylyl N,N-dimethyl phorphoramidate These are given as illustrative of the numerous compounds which can be prepared in accordance with the process of the invention. Numerous other compounds would be obvious to one skilled in the art, particularly in view of the numerous phosphoramidic dihalide and phenol reactants listed hereinbefore.

The compounds prepared by the process of the present invention are particularly useful as flame retardant additives for various polymer systems. Effective flame retardant results can be obtained in polyurethanes of both flexible and rigid, foamed and non-foamed varieties, cellulosics including wood, wood fiber, wool, and cotton; modified celluloses such as cellulose acetate and rayon; polyamides (nylons) olefin polymers such as polyethylene and polypropylene; natural and synthetic rubbers such as SBR (styrene-Butadiene-rubber);

epoxy polymers; polyesters of the saturated and unsaturated varieties, such as polyethylene terephthalate; acrylic and methacrylic polymers including the derivative polymers of the esters, amides and nitriles; polyvinyl acetals such as polyvinyl acetal and polyvinyl butryal; phenolics such as phenol-formaldehyde polymers; bitumens or mixtures of hydrocarbons of natural or pyrogenous origin including asphalts and pitch; poly(-phenylene oxide) polymers from 2,6-disubstituted phenol such as 2,6-dimethylphenol; polyethers such as polyethylene or polypropylene glycol and the glycerol and thioether derivatives; vinyl polymers such as vinyl acetate, vinyl halides (vinyl chloride), vinyl ethers (vinyl ethyl ether) vinyl esters of halogenated carboxylic acids (vinyl chloroacetate), aryl vinyls (styrenes), halostyrenes (chlorostyrene), polyvinyl alcohol polymers, as well as the copolymers of such vinyl polymers.

All types of polymer materials both synthetic as well as naturally derived can thus be effectively treated with the fire retardant additives of the present invention in order to reduce or retard the flammability characteristics of the polymer materials.

The compounds of the present invention are, in general, additive type flame retardants which can be admixed with or padded or coated onto the polymer to be flame retarded. The method of application would be obvious to one skilled in the art of any specific polymer system.

These compounds are in such amount as to provide the desired flame retardancy. Generally loadings of from 1 to 25%, by weight, depending on the polymer system, are effective.

The invention will be further illustrated in the Examples which follow.

EXAMPLE 1

16.2 grams (0.10 mole) of dimethyl phosphoramidic dichloride were admixed with 20 grams (0.22 mole) of phenol at 10°C. in a flask containing 200 milliliters methyl isobutyl ketone and which was cooled by an ice water bath. Pellets of sodium hydroxide were ground and slowly added to the reaction mixture until about 10 grams has been added. The maximum temperature was 42°C. The ice bath was removed and 1 more gram of sodium hydroxide was added. No temperature rise was noted and the mixture was stirred overnight. The product was washed with water, the included sodium chloride by-product are separated and the methyl isobutyl ketone removed by distillation. The product yield was 26.4 grams or 91%. Gas chromotograph indicated 98.8% of the yield was true diphenyl N,N-dimethyl phosphoramidate indicating an actual final product yield of 90%.

It has been found that the quantities of water present during the reaction are critical to the production of high yields of O,O'diphenyl-N,N-dimethyl phosphoramidate. If a 25% solution of sodium hydroxide in water is used instead of pure sodium hydroxide, yields of less than 90% are obtained as illustrated in the following example.

EXAMPLE 2

Preparation of O,O'-diphenyl N,N-dimethyl phosphoramidate 322 grams (2 moles) of dimethyl phosphoramidic dichloride and 385.4 grams (4.10 mole) of phenol are added to a 5 liter flask containing about 2 liters of methyl isobutyl ketone as solvent.

The dimethyl phosphoramidic dichloride was prepared by reacting 6000 grams (38.5 mole) of phosphorus oxychloride with 505 grams (11.2 mole) of dimethyl amine. The gaseous anhydrous dimethyl amine was added to the phosphorus oxychloride and the temperature of the reaction mixture was maintained with an ice water bath. The reaction mixture was then heated for 10 hours to drive off HCl. The product was purified by distillation.

The dimethyl phosphoramidic dichloride/phenol mixture was then stirred and the temperature of the reaction was maintained below 42°C. with external cooling. 352 grams (2.2 mole) of sodium hydroxide in a 25% solution was added slowly to maintain temperature and the mixture was stirred an additional hour. The reaction mixture separated into three phases, a sodium chloride salt phase, a water phase, and a methyl isobutyl ketone phase. The liquid phases were decanted and the sodium chloride was washed two times with 50 milliliters of methyl isobutyl ketone. The methyl isobutyl ketone washings were combined with the other liquid phases and the methyl isobutyl ketone phase was separated from the aqueous phase. The methyl isobutyl ketone phase containing the reaction product was then washed four to six times with portions of water which in toto was less in volume than the volume of the methyl isobutyl ketone solution. The methyl isobutyl ketone was then stripped and the product purified by distillation. The yield of product which was identified by a gas chromotagraph as O,O'-diphenyl-N,N-dimethyl phosphoramidate was 23.4%. The intermediate compound, phenyl N,N-dimethyl phosphoramidochloridate comprised 48.4 % of the product.

EXAMPLE 3

The following compounds are prepared by the procedures of Examples 1 and 2 by substituting the appropriate dialkyl phosphoramidic dihalide and phenol reactants therein:

a. O,O-dicresyl N,N-dimethyl phosphoramidate using N,N-dimethyl phosphoramidic dichloride and cresylic acid.

b. O,O-dixylyl N,N dimethyl phosphoramidate using N,N dimethyl phosphoramidic dichloride and xylenol.

c. O,O-diphenyl N,N-diethyl phosphoramidate using N,N-diethyl phosphoramidic dichloride and phenol.

EXAMPLE 4

Flame retardant compositions utilizing the compounds prepared by the process of the present invention are prepared and tested as follows:

Cellulose Acetate - the flame retardant compositions of examples 1 and 2 are mixed in a 20 weight percent solution of cellulose acetate in an 80/20 acetone/methanol solvent system. The solution is then cast into a 15 mil sheet, and air dried for 1 hour followed by an oven drying at 70°–80°C. for about an hour. The fire retardant is used in such an amount that the final dry film contains a given percentage of fire retardant based on the dry weight of the acetate. Strips are then cut from the film and ignited in a bunsen burner flame.

Viscose Rayon - weighed samples of fire retardant of examples 1 and 2 are dissolved in a solvent such as dichloromethane and known weights of viscose rayon staples are alternately dipped into the solution and air dried until all the solution is consumed. The treated staples are then air dried over night, manually carded for homogeneity and ingited in a bunsen burner flame.

The results of the flame retardancy tests are shown in Table I below.

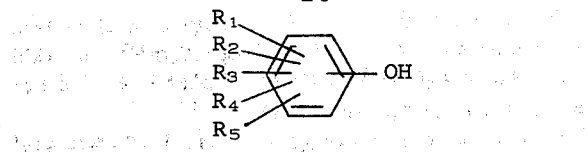

TABLE I

| COMPOUND STRUCTURE | HYDROLYSIS (Resistance) | VISCOSE RAYON (5 grams) Grams of Flame Retardant | | | CELLULOSE ACETATE Grams of Flame Retardant | | |
|---|---|---|---|---|---|---|---|
| | | 0.15 | 0.30 | 0.50 | 2.5% | 5.0% | 10% |
| $(\phi O)_2 P(O)N(CH_3)_2$ | GOOD | B/C | C/D | — | — | D | D |
| $(\phi O)_2 P(O)NH_2$ | UNSTABLE IN CAUSTIC SOLUTION | B | B | — | B/C | C | D |

A = Flammable
B = Partially Flammable
C = Partially Self-Extinguishing
D = Self-Extinguishing

EXAMPLE 5

A 10% solution of polypropylene oxide alternatively named poly(2,6-dimethylphenylene oxide) obtained commercially under the trademark "PPO" in benzene compounds of Examples 1 and 2 was prepared. The solution was poured into petri dishes and dried at room temperature for approximately 24 hours. The flame retardants compound of Examples 1 and 2 were admixed with the solution in an amount sufficient to provide loadings in the dried film of from 5 to 30% in increments of 5%. The so prepared samples were then inserted into a bunsen burner flame to determine flame retardancy. The samples were found to have flame retardant properties greater than an untreated control sample and better than the presently used triphenyl phosphate. The higher loadings were more effective than the lower loadings.

TABLE II

| Polyphenylene Oxide | Loading | |
|---|---|---|
| Fire Retardant | 5% | 10% |
| (Phenyl-O)$_2$P(O)N(Me)$_2$ | just self exting. | Self extinguishing |
| Blank (Control) | burns | Burns |

EXAMPLE 6

A polyurethane foam was prepared utilizing the following composition:

Grams:
200 - Varanol R. S. 450 hydroxyl No. 450
225.9 - Polymethylene polyphenyl isocyanate (PAPI)
50 - product of Example 5 (O,O-diphenyl N,N dimethyl phosphoramidate)
4 - silicone surfactant DC-193
2 - dimethylethanolamine
70 - trichlorofluormethane
1.5 - dibutyl tin dilaurate These ingredients yielded a foam having a rise time of 55 seconds, and a density of 2.09 lb/cu.ft. The foam was of good appearance, and cell size, and over 94% of the cells were closed. The foam was self-extinguishing by ASTM test method D-1692.

The invention is defined in the claims which follow. What is claimed is:

1. A method for preparing O,O-diaryl N,N-dialkyl phosphoramidates which comprises reacting a phenol of the formula:

wherein $R_1$-$R_5$ independently represent hydrogen, $C_1$-$C_4$ alkyl and hydroxy alkyl, chlorine or bromine with an N,N-dialkyl phosphoamidic halide of the formula:

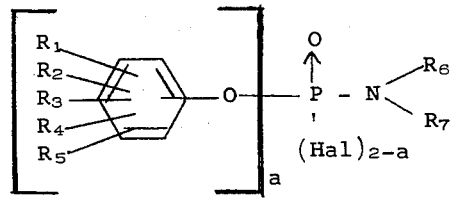

wherein $R_6$ and $R_7$ represent the same or different $C_1$-$C_4$ alkyl radicals, $R_1$-$R_5$ are as defined hereinbefore, a is a number equal to 1 or 0 and Hal is a halogen of chlorine or bromine; said reaction being conducted in the presence of an alkali metal or an alkaline earth metal hydroxide in an amount at least stoichiometrically equivalent to the phenol, said hydroxide being used in concentrations of from 50 to 100% by weight, the remainder being composed of water; and a substantially water-insoluble, water-immiscible, non-hydroxylic, polar ketone which is a solvent for said phenol, said halide and phosphoramidate; said ketone being selected from the group consisting of ketones defined by the formula:

$R_xC(O)R_y$ wherein $R_x$ represents a $C_1$-$C_4$ alkyl group and $R_y$ represents a $C_3$-$C_8$ alkyl and alicyclic ketones of the formula:

$CH_2(CH_2)_nC\ O$ wherein $n$ is an integer of 4 or 5 and the lower alkyl substituted derivatives thereof; the total number of carbon atoms of said ketone not exceeding 10.

2. The method as recited in claim 1 wherein said N,N dialkyl phosphramidic halide is N,N-dimethyl phosphoramidic dichloride.

3. The method as recited in claim 1 wherein said solvent is methyl isobutyl ketone.

4. The method as recited in claim 1 wherein said hydroxide is sodium hydroxide.

5. The method as recited in claim 1 wherein said hydroxide is added in the solid state to a substantially water free reaction mixture of phenol.

6. The method as recited in claim 5 wherein said hydroxide is sodium hydroxide.

7. The method as recited in claim 1 wherein said phenol is phenol.

8. The method as recited in claim 1 wherein said phosphoramidic halide is a phosphoramidic dihalide and approximately 2.05 moles of phenol is used per mole of phosphoramidic dihalide.

9. The method as recited in claim 1 wherein said sodium hydroxide is used in the form of flakes.

10. The method as recited in claim 1 wherein the temperature of reaction is within the range of from about 25°C. to about 60°C.

* * * * *

UNITED STATES PATENT AND TRADEMARK OFFICE
CERTIFICATE OF CORRECTION

PATENT NO. : 3,937,765
DATED : February 10, 1976
INVENTOR(S) : Arthur D. F. Toy and Kenneth L. Eilers It is certified that error appears in the above-identified patent and that said Letters Patent are hereby corrected as shown below:

<u>Column 1, line 49</u>

Change "combination" to -- contamination --;

<u>Column 5, line 1</u>

"$CH_2(CH_2)_nCO$" should be -- $\overline{CH_2(CH_2)_nCO}$ --;

<u>Column 5, line 47</u>

Change "a" to -- as --;

<u>Column 10, line 51</u>

"$CH_2(CH_2)_nCO$" should be -- $\overline{CH_2(CH_2)_nCO}$ --.

Signed and Sealed this eighth Day of June 1976

[SEAL]

Attest:

RUTH C. MASON
*Attesting Officer*

C. MARSHALL DANN
*Commissioner of Patents and Trademarks*